(12) United States Patent
Kinugasa et al.

(10) Patent No.: US 10,525,287 B2
(45) Date of Patent: Jan. 7, 2020

(54) PARTICLE BEAM TREATMENT APPARATUS WITH CABLE LENGTH ADJUSTER

(71) Applicants: KABUSHIKI KAISHA TOSHIBA, Minato-ku (JP); Toshiba Energy Systems & Solutions Corporation, Kawasaki-shi (JP)

(72) Inventors: Kunihiko Kinugasa, Yokohama (JP); Kiyohiko Kitagawa, Yokohama (JP); Yuuji Takiguchi, Yokohama (JP); Kazutaka Maeta, Yokohama (JP)

(73) Assignees: KABUSHIKI KAISHA TOSHIBA, Minato-ku (JP); Toshiba Energy Systems & Solutions Corporation, Kawasaki-shi (JP)

( * ) Notice: Subject to any disclaimer, the term of this patent is extended or adjusted under 35 U.S.C. 154(b) by 0 days.

(21) Appl. No.: 16/153,863

(22) Filed: Oct. 8, 2018

(65) Prior Publication Data
US 2019/0126073 A1    May 2, 2019

(30) Foreign Application Priority Data
Oct. 27, 2017    (JP) .................................. 2017-207832

(51) Int. Cl.
*A61N 5/10*    (2006.01)

(52) U.S. Cl.
CPC ......... *A61N 5/1081* (2013.01); *A61N 5/1048* (2013.01); *A61N 2005/1074* (2013.01); *A61N 2005/1087* (2013.01)

(58) Field of Classification Search
CPC .. B65H 2701/34; B65H 57/14; A61N 5/1081; A61N 5/1048; A61N 2005/1074; A61N 2005/1087
See application file for complete search history.

(56) References Cited

U.S. PATENT DOCUMENTS

| | | | |
|---|---|---|---|
| 4,960,544 A | 10/1990 | Van Putte et al. | |
| 5,993,373 A | 11/1999 | Nonaka et al. | |
| 8,848,861 B2 * | 9/2014 | Hall | A61B 6/03 378/8 |

(Continued)

FOREIGN PATENT DOCUMENTS

| | | |
|---|---|---|
| EP | 1 402 923 A1 | 3/2004 |
| JP | 6-104839 B2 | 12/1994 |

(Continued)

*Primary Examiner* — Brooke Purinton
(74) *Attorney, Agent, or Firm* — Oblon, McClelland, Maier & Neustadt, L.L.P.

(57) ABSTRACT

A particle beam treatment apparatus includes: a gantry configured to axially rotate in a state where an irradiation port for a beam is fixed to a body of the rotating gantry; a moving floor that is provided inside the gantry, is configured by annually connecting a plurality of plates with each other in a freely bendable manner, accommodates at least a part of a bed fixed from a stationary system, and rotates together with the gantry in a state of causing the irradiation port to penetrate the moving floor; a cable configured to be connected to a device fixed to the moving floor and be wired to outside of the gantry in a state of passing through the gantry; and an adjuster configured to adjust length of the cable wired inside the gantry when the gantry axially rotates.

6 Claims, 5 Drawing Sheets

(56) References Cited

U.S. PATENT DOCUMENTS

2014/0121441 A1 5/2014 Huber et al.
2017/0001041 A1 1/2017 Yamashita et al.

FOREIGN PATENT DOCUMENTS

| JP | 11-47287 | 2/1999 |
| JP | 2001-353228 | 12/2001 |
| JP | 2011-156263 | 8/2011 |
| JP | 2014-147451 A | 8/2014 |
| JP | 2017-55958 A | 3/2017 |

* cited by examiner

US 10,525,287 B2

PARTICLE BEAM TREATMENT APPARATUS WITH CABLE LENGTH ADJUSTER

CROSS-REFERENCE TO RELATED APPLICATION

This application claims the benefit of priority of Japanese Patent Application No. 2017-207832, filed Oct. 27, 2017, the entire contents of which are incorporated herein by reference.

FIELD

Embodiments of the present embodiment generally relate to a particle beam treatment apparatus equipped with a gantry.

BACKGROUND

A particle beam therapy is widely practiced as treatment of irradiating a lesion area (e.g., cancer) of a patient with a particle beam such as a proton beam and a carbon ion beam. As one of such particle beam therapies, there is a known technique in which a patient lying on a treatment bed is positioned and irradiated with a particle beam in a treatment room formed inside a large rotation mechanism (hereinafter, referred to as a gantry).

In a particle beam treatment apparatus having such a gantry, by rotating the irradiation port fixed to the gantry or displacing the treatment bed in the treatment room, a lesion area of a patient is irradiated with a particle beam from an arbitrary direction.

The treatment room formed inside the gantry is formed by a moving floor that is configured of a horizontally flat floor surface and the other surfaces having an arch shape along the inner circumference of the gantry so as to form a D-shaped cross-section regardless of the rotational position of the gantry.

The treatment room is formed by the moving floor in which the horizontally flat floor surface and the arch surface are maintained while the irradiation port is fully rotated around (i.e., by 360°). This improves workability of a technician in the internal space of the treatment room and reduces the feeling of mental pressure of the patient lying on the treatment bed.

[Patent Document 1] Japanese Unexamined Patent Application Publication No. 1999-47287

[Patent Document 2] Japanese Unexamined Patent Application Publication No. 2001-353228

[Patent Document 3] Japanese Unexamined Patent Application Publication No. 2011-156263

When a device is installed on this moving floor, a cable for inputting and outputting signals to this device and another cable for supplying electric power pass through the through-hole provided in the gantry and extend to the outside thereof.

Since the moving floor has a D-shaped cross-section as described above, the distance between the position of the device provided on the moving floor and the position of the through-hole provided in the gantry depends on the rotation angle of the gantry and is not constant.

Thus, when the cables are caused to rotate in conjunction with the rotation of the gantry, as the gap between the moving floor and the gantry becomes narrower, there is a higher possibility that an extra length of each cable is generated in this gap and the cable(s) is tangled so as to be broken or the stable rotation of the gantry is inhibited.

In view of the above-described problems, it is an object of embodiments of the present invention to provide a particle beam treatment apparatus which is excellent in stability of rotating operation by devising the wiring of the cable(s) connected to the device installed on the moving floor.

DETAILED DESCRIPTION

Hereinbelow, embodiments of the present invention will be described with reference to the accompanying drawings.

Figure 1:
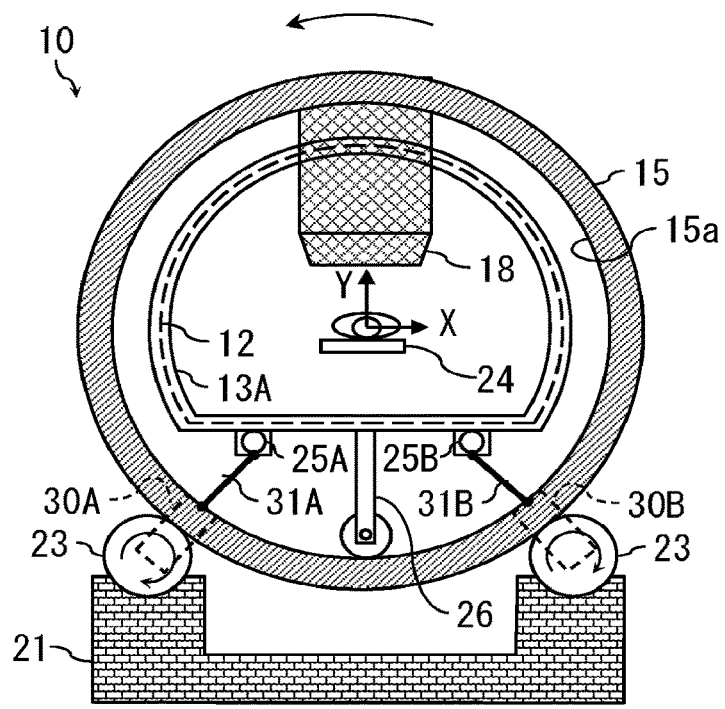
FIG. 1 is an X-Y cross-sectional view of a particle beam treatment apparatus according to an embodiment of the present invention.
Figure 2:
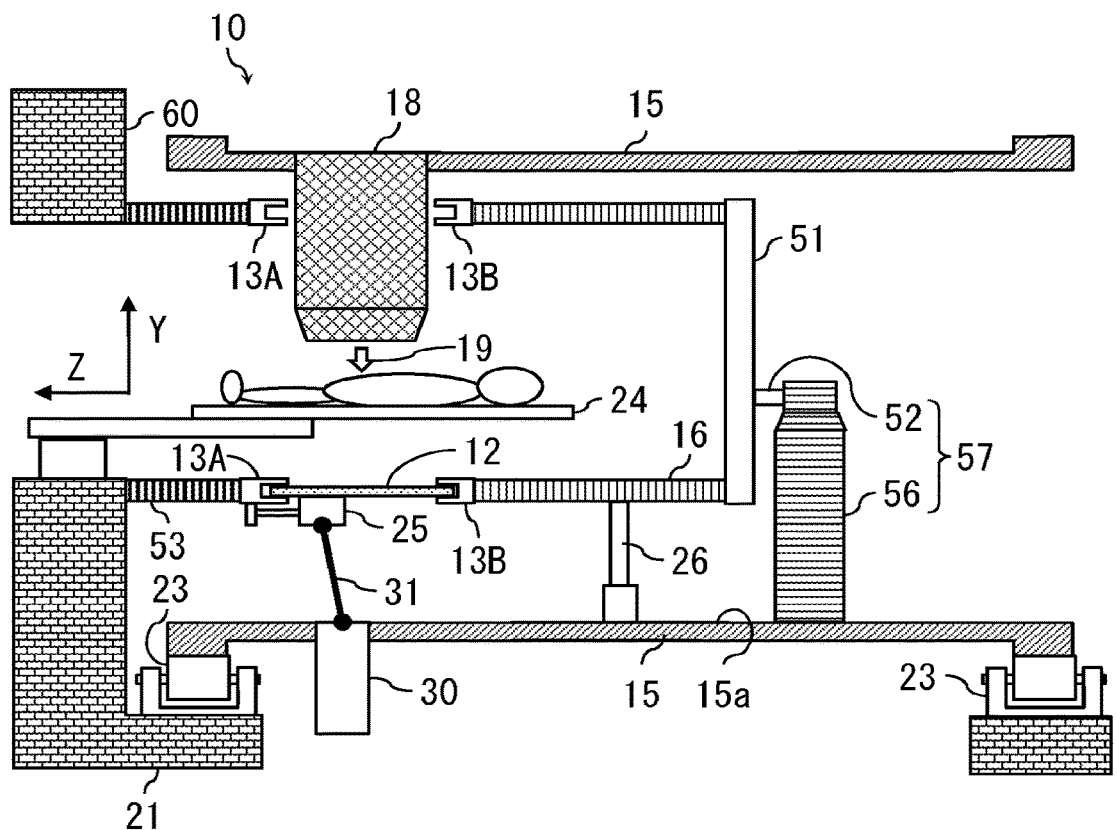
FIG. 2 is a Y-Z cross-sectional view of the particle beam treatment apparatus according to the embodiment.
Figure 3:
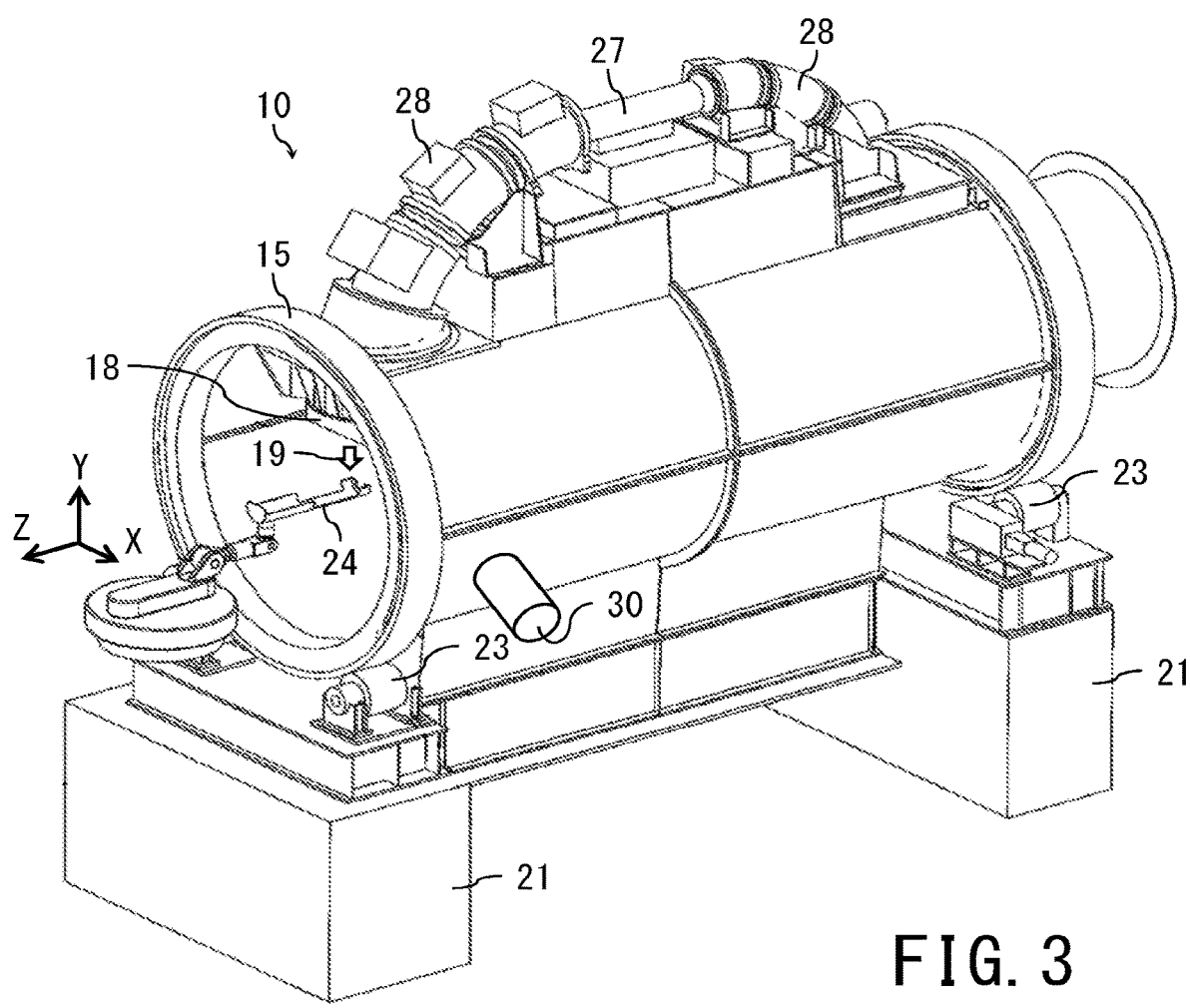
FIG. 3 is a perspective view illustrating an appearance of the particle beam treatment apparatus according to the embodiment.

FIG. 1 and FIG. 2 are an X-Y cross-sectional view and a Y-Z cross-sectional view of the particle beam treatment apparatus 10 according to the present embodiment, respectively. FIG. 3 illustrates the appearance of the particle beam treatment apparatus 10.

The particle beam treatment apparatus 10 includes a gantry 15, a moving floor 12, cables 31A and 31B (hereinafter, collectively denoted as 31, as needed), and adjusters 30A and 30B (hereinafter, collectively denoted as 30, as needed). The gantry 15 axially rotates under the state where an irradiation port 18 for a beam 19 is fixed to the body of the gantry. The moving floor 12 is provided inside the gantry 15, is formed by annularly joining plural plates 11 to each other so as to be freely bendable, accommodates at least a part of a bed 24 fixed from a stationary system 21, and rotates together with the gantry 15 under the state where the irradiation port 18 penetrates the moving floor 12. The cables 31A and 31B are respectively connected to driving devices 25A and 25B (hereinafter, collectively denoted as 25, as needed) fixed to the moving floor 12, pass through the gantry 15, and are wired outside the gantry 15. The adjuster 30A and 30B respectively adjust the length of the cable 31A and the length of the cable 31B to be wired inside the gantry 15 when the gantry 15 axially rotates, and eliminates excessive tension or looseness of the cables 31.

The particle beam treatment apparatus 10 further includes a tunnel structure 16 and a rotation supporter 57. The tunnel structure 16 has a horizontal floor surface and an arch-shaped ceiling, and has an internal space in which at least a part of the bed 24 is accommodated. The rotation supporter 57 rotationally displaces the tunnel structure 16 with respect to the inner side surface 15a of the gantry 15 so as to bring the tunnel structure 16 into a stationary state as viewed from the stationary system 21 regardless of the axial rotation of the gantry 15.

As shown in FIG. 3, the gantry 15 is a large-sized structure having a cylindrical shape in general, and rotates around the rotation axis (i.e., Z-axis) under rotation driving of plural rotation drivers 23, which are in contact with the outer peripheral surfaces of both edge ends of the gantry 15. The weight of the gantry 15 is supported by a foundation 21 (stationary system) via the rotation drivers 23.

The gantry 15 axially rotates under the state where the bed 24 fixed to the stationary system is disposed inside and the irradiation port 18 for the beam 19 is fixed to the body.

In addition to the irradiation port 18 for the particle beam 19, the gantry 15 is provided with many control devices and structures such as a beam control system 27 and beam deflection electromagnets 28.

The particle beam 19 is generated by accelerating ions (heavy particles or proton ions generated by a non-illustrated ion source) with a linear accelerator and further making the accelerated ions incident on a non-illustrated circular accelerator to increase the energy of the ions to a preset value.

Thereafter, the particle beam 19 outputted from the circular accelerator is made incident on a non-illustrated beam transportation system from the extension line of the rotation axis Z of the beam transportation system that is provided so as to rotate integrally with the gantry 15.

The irradiation port 18 is inserted toward the inside of the gantry 15 and rotates together with the gantry 15 by ±180° around the bed 24.

The trajectory of the particle beam 19 made incident on the beam transport system is bent by the deflection electromagnets 28, and then the particle beam 19 is outputted from the irradiation port 18 such that a patient lying on the bed 24 is irradiated with this particle beam 19 from any direction of 0° to 360°.

This bed 24 has a base fixed to the foundation (stationary system) 21 on the building side, moves inside the gantry 15, and positions the lesion area of the patient at the irradiation position of the particle beam 19.

After the lesion area is irradiated with the particle beam 19, the particle beam 19 decreases its speed by losing kinetic energy when passing through the patient's body, and suddenly stops when it falls to a certain speed by receiving a resistance which is approximately inversely proportional to the square of speed.

In the vicinity of the stop point of the particle beam 19, high energy called a Bragg peak is emitted. Since the bed 24 is positioned such that the release position of this Bragg peak coincides with the lesion area, only the tissues of the lesion area are killed and treatment with less damage of normal tissues is executed.

Figure 4:
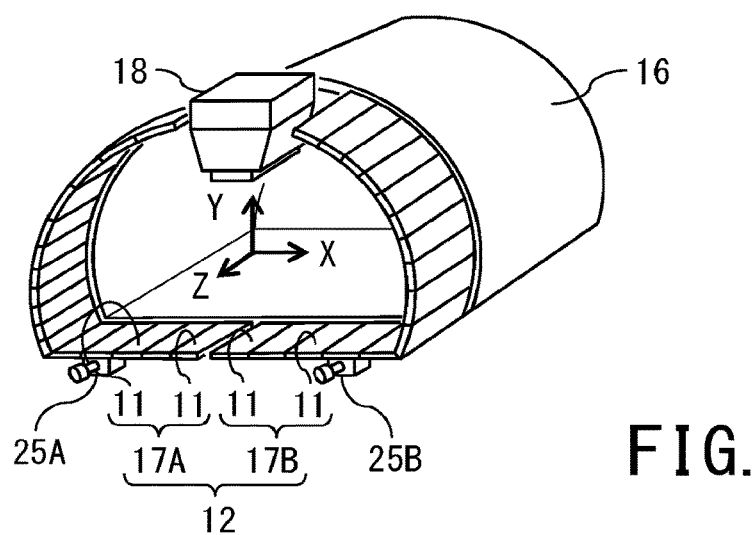
FIG. 4 is an overall perspective view illustrating the moving floor and the tunnel structure.

FIG. 4 is a schematic perspective view focusing on the moving floor 12 and the tunnel structure 16. Each of the plates 11 constituting the moving floor 12 is desired to have large flexural rigidity in the longitudinal direction and to be lightweight. The multiple plates 11 are joined to each other at the side edge portions thereof so as to be freely bendable.

The moving floor 12 can rotate in conjunction with the rotation of the gantry 15 by causing the irradiation port 18 to pass through the opening that is provided on a part of the moving floor 12.

A first rail 13A and a second rail 13B are slidably engaged at one end and the opposite end of the moving floor 12, respectively. Each of the first rail 13A and the second rail 13B has a closed track composed of a circular arc and a straight line.

Thus, the inner space of the moving floor 12 forms a tunnel shape surrounded by a flat horizontal floor and an arch-shaped ceiling, and the moving floor 12 can rotate around the rotation axis Z while keeping the tunnel shape stationary.

The moving floor 12 does not have to be wide in the direction of the rotation axis (i.e., Z-axis direction) because space of the treatment room is sufficiently secured due to the presence of the tunnel structure 16 as described below. Hence, the moving floor 12 can be designed to be lightweight and have high mechanical rigidity, and thus the rotational motion of the moving floor 12 can be smoothly implemented while maintaining quietness.

The first rail 13A is supported at one end of a hollow body 53, the other end of which is connected to an opening of a vertical wall surface (stationary system) of the foundation 21 fixing the bed 24.

The support of the first rail 13A from the foundation 21 is not limited to the illustrated method. For instance, the first rail 13A may be fixed to a non-illustrated supporter, which is rotatably provided with respect to the inner peripheral surface of the gantry 15 and is supported by the vertical wall surface (stationary system) 60 of the foundation 21, in such a manner that the first rail 13A is indirectly supported by the stationary system.

The second rail 13B is fixed to the periphery of the tunnel structure 16 that substantially matches in sectional shape with the second rail 13B. The second rail 13B is disposed so as to face the first rail 13A with the irradiation port 18 interposed between the first and second rails 13A and 13B, and is engaged with the other end of the moving floor 12.

It is sufficient that the distance between the first and second rails 13A and 13B is slightly wider than the width of the irradiation port 18 interposed between them.

By reducing the length of the moving floor 12 in the direction of the rotation axis (Z-axis) in the range satisfying the above condition, both of weight reduction and improvement of mechanical rigidity can be achieved for the moving floor 12 rotating together with the gantry 15.

In the tunnel structure 16, a panel 51 is provided on the opposite side of the second rail 13B so as to close the opening. The panel 51 is supported by a rotation shaft 52 of the rotation supporter 57. The rotation shaft 52 matches the rotation axis Z of the gantry 15 in terms of position and orientation and freely rotates.

The tunnel structure 16 is not an indispensable component. Instead of providing the tunnel structure 16, the movable floor 12 may be extended to the panel 51 in substitution for the tunnel structure 16.

The rotation supporter 57 rotationally displaces the rotation shaft 52 that pivotally supports the tunnel structure 16 from a stand 56 fixed to the inner side surface 15a of the gantry 15. As a result, the tunnel structure 16 becomes stationary with respect to the stationary system in such a manner that the flat floor surface always remains horizontal without depending on the rotational displacement of the gantry 15.

In the stationary system, the rotation shaft 52 of the rotation supporter 57 is rotationally displaced in the direction opposite to the rotational direction of the gantry 15. Consequently, the rotation supporter 57 is fixed to the inner side surface 15a of the gantry 15, and thus the tunnel structure 16 is kept in the stationary state even when the irradiation port 18 rotates with respect to the stationary system.

Further, the rotation supporter 57 is provided with a support member 26 that supports its own weight in the vertical direction. One end of the support member 26 is fixed to the tunnel structure 16 or the panel 51, and the other end of the support member 26 frictionlessly contacts the inner side surface 15a of the gantry 15 and rotates in the circumferential direction. Note that the rotation shaft 52 of the rotation supporter 57 may be freely rotatable in addition to being driven and rotated by, e.g., a motor.

Although a description has been given of the case where the rotation supporter 57 is composed of the rotation shaft 52 and the stand 56 in the present embodiment, the rotation supporter 57 is not limited to such an aspect. It is possible to adopt any rotation supporter 57 that can support the tunnel structure 16 and the moving floor 12 configured to be rotationally displaced with respect to the inner side surface 15a of the gantry 15.

The moving floor 12 is composed of at least two separate bodies 17A and 17B such that the connection of the plural plates 11 is divided at the position where the irradiation port 18 penetrates the moving floor 12. The separate bodies 17A and body 17B respectively include driving devices 25A and 25B (hereinafter, collectively referred to as the driving devices 25, as needed) for causing the respective closed tracks of the first and second rails 13A and 13B to run independently of each other.

Specifically, a rack-and-pinion mechanism can be adopted as each of the driving devices 25A and 25B. In this case, a motor for rotating a small-diameter circular gear called a pinion is provided on the plates 11 constituting each of the separate bodies 17A and 17B. At least one of the first rail 13A and the second rail 13B is provided with a toothed rack. When rotational force is applied to the combination of the rack and the pinion, the rotational force is converted into linear force in the longitudinal direction of the rack, and the separate bodies 17A and 17B of the moving floor 12 move along the respective closed tracks of the first and second rails 13A and 13B.

The driving devices 25A and 25B are not limited to the rack-and-pinion mechanism and may be configured as any other mechanism as long as it can cause the separate bodies 17A and 17B to run independently of each other on the closed tracks of the first and second rails 13A and 13B.

Figure 5A:
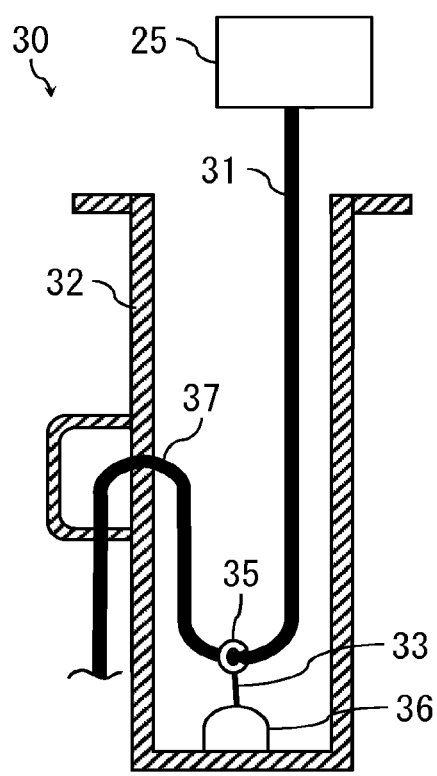
FIGS. 5A and 5B are schematic cross-sectional views illustrating the operation of each cable-length adjuster.
Figure 5B:
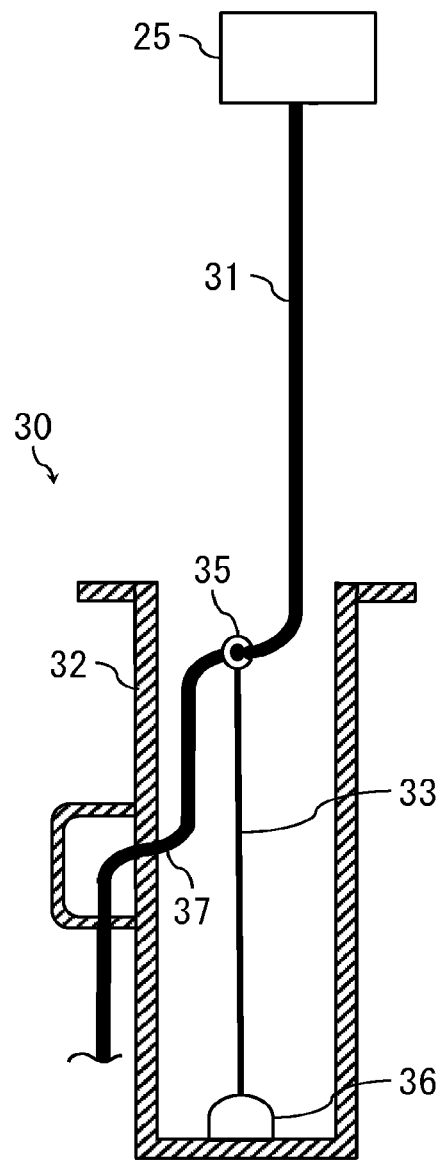

The configuration of the cable-length adjusters 30 will be described with reference to FIG. 5A and FIG. 5B. FIG. 5A illustrates the state of one of the cables 31 when the driving device 25 fixed to the moving floor 12 approaches the corresponding adjuster 30A or 30B, and FIG. 5B illustrates the state of one of the cables 31 when the driving device 25 is separated from the corresponding adjuster 30A or 30B.

Each of the adjusters 30 includes a casing 32, a wire 33, and a wheel 36. The casing 32 is provided at such a position of the gantry 15 that the cable 31 passes through the gantry 15, and accommodates this cable 31 by the cable 31. The wire 33 holds a part of the cable 31 inside the casing 32 by using a towing bracket 35 provided at the tip. The wheel 36 is provided in the casing 32, winds the wire 33 from its end, and rotates in the forward/reverse direction according to the displacement of the towing bracket 35.

The cable 31 on the side opposite to the connection side of the driving device 25 is fixed in the state of penetrating the side peripheral wall of the casing 32 in the fixing portion 37, and is guided to the outside of the casing 32.

The rotation of the wheel 36 is resiliently biased in the direction in which the wire 33 is wound (in the direction in which the cable 31 is pulled in). As a result, when the driving device 25 approaches the opening of the adjuster 30 as shown in FIG. 5A, the cable 31 is pulled in by the towing bracket 35 and housed inside the casing 32.

Conversely, when the driving device 25 moves away from the opening of the adjuster 30 as shown in FIG. 5B, the cable 31 is pulled out of the casing 32 against the biasing force of the towing bracket 35. Note that each cable 31 can be pulled out in any direction.

As another embodiment of the wheel 36, a drive-controlled motor may be connected for driving and controlling the rotation of the wheel 36.

By configuring the adjusters 30 in the above-described manner, the length of the cables 31 wired inside the gantry 15 configured to axially rotate is adjusted, and excessive tension and slackness of the cable 31 can be eliminated.

Although driving devices configured to cause the separate bodies 17A and 17B constituting the moving floor 12 to run are exemplified as the driving devices 25 of the present embodiment, the driving devices 25 are not particularly limited to the above-described type. Each of the driving devices 25 may be a device such as a sensor and an actuator provided on the moving floor 12 in some cases.

There are also cases where plural driving devices 25 are provided on the moving floor 12. In this case, each of the cables 31 is configured by bundling non-illustrated plural lines connected to the respective plural driving devices 25 into one and covering the bundled lines. As described above, the lines constituting the cable 31 are for supplying electric power to the driving devices 25, transmitting a detection signal of a sensor, or transmitting a control signal of the actuator, for instance.

Further, the casing 31 may be made of a transparent material such that the shape of the cable 31 to be accommodated in the casing 31 can be visually recognized from the outside.

The operation of the moving floor 12 and the cable-length adjusters 30 (30A, 30B) will be described with reference to FIG. 6 to FIG. 9.

The flat horizontal floor surface of the moving floor 12 to be rotated does not generate a gap, and it is necessary to secure safety of a technician moving in and out of the moving floor 12.

For this reason, when the respective edges 14A and 14B of the separate bodies 17A and 17B are positioned on the flat horizontal floor surface, the driving devices 25A and 25B for moving the separate bodies 17A and 17B performs setting such that the edges 14A and 14B contact with each other or are in contact with the irradiation port 18. In this manner, the driving devices 25A and 25B controls the separate bodies 17A and 17B such that a gap is not generated on the flat horizontal floor surface. The edges 14A and 14B located in the arch-shaped ceiling form a gap and allow the inner surface 15a of the gantry 15 to be exposed from the opening of the moving floor 12 formed on the arch side.

As a result, as shown in FIG. 6 to FIG. 9, the distance between the driving devices 25A and 25B and the corresponding adjusters 30A and 30B changes depending on the rotational position of the irradiation port 18.

Figure 6:
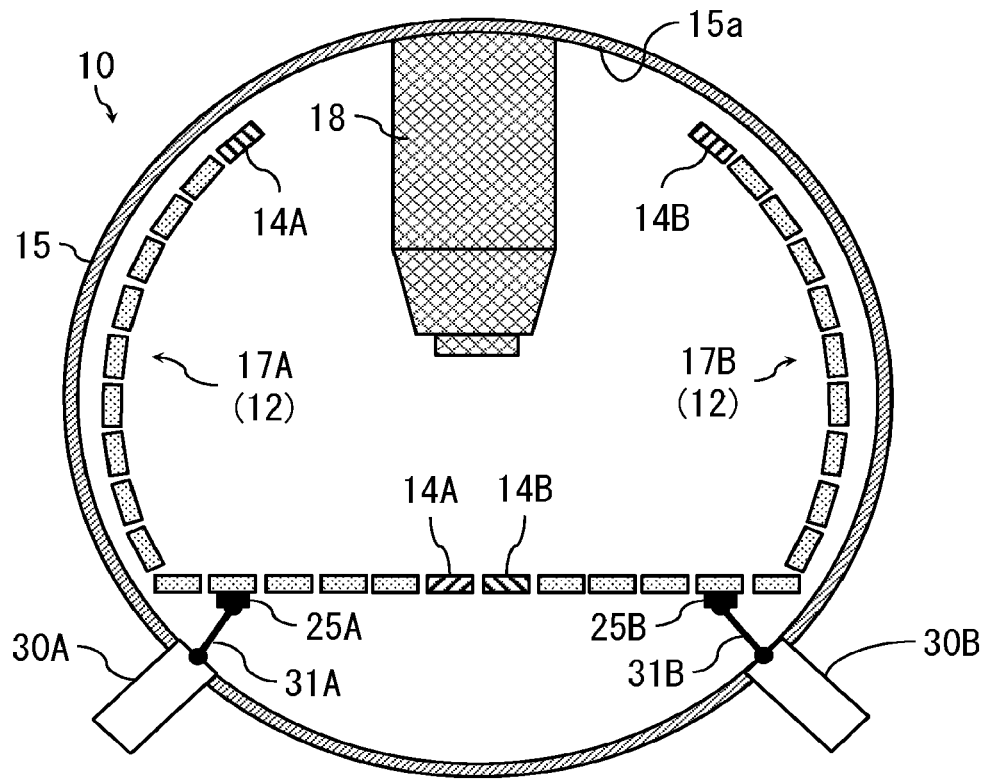
FIG. 6 is a schematic cross-sectional view illustrating the operation of the moving floor and the cable-length adjusters.

As shown in FIG. 6, consider a case where the rotation angle of the gantry 15 is set to 0° and the irradiation port 18 is positioned directly above the bed 24. In this case, by causing the respective edges 14A and 14B of the separate bodies 17A and 17B to contact each other on the horizontal floor surface, the horizontal flat floor surface of the moving floor 12 is formed without forming an opening on the floor surface.

In this state, both of the driving devices 25A and 25B are positioned on the horizontal floor surface and the cables 31A and 31B are both pulled out halfway from the respective adjusters 30A and 30B.

Figure 7:
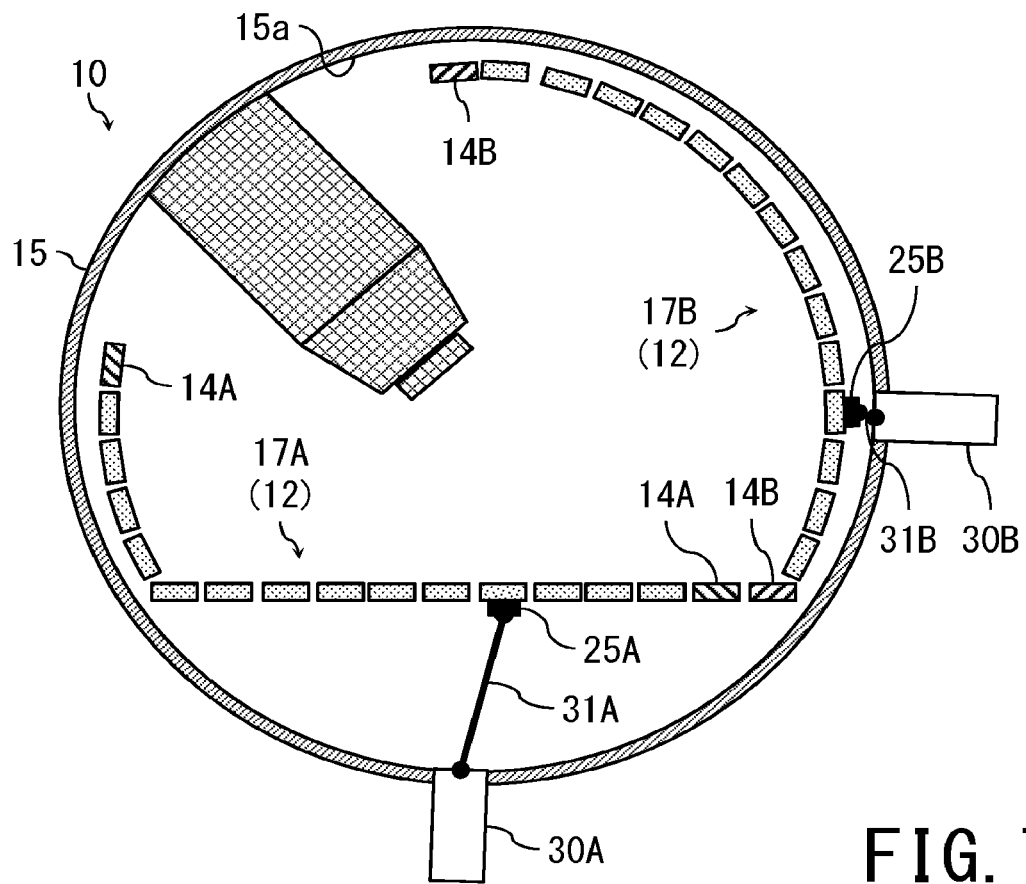
FIG. 7 is another schematic cross-sectional view illustrating the operation of the moving floor and the cable-length adjusters.

Next, as shown in FIG. 7, consider a case where the rotation angle of the gantry 15 is set to 45° and the irradiation port 18 is positioned obliquely above the bed 24. Also in this case, by causing the respective edges 14A and 14B of the separate bodies 17A and 17B to contact each other on the horizontal floor surface, the horizontal flat floor surface of the moving floor 12 is formed without forming an opening on the floor surface.

In this state, the driving device 25A is positioned on the horizontal floor surface and the corresponding cable 31A is almost entirely pulled out from adjuster 30A toward the rotational center, while the driving device 25B is positioned at the arch-shaped ceiling and the corresponding cable 31B is almost accommodated in the adjuster 30B.

Figure 8:
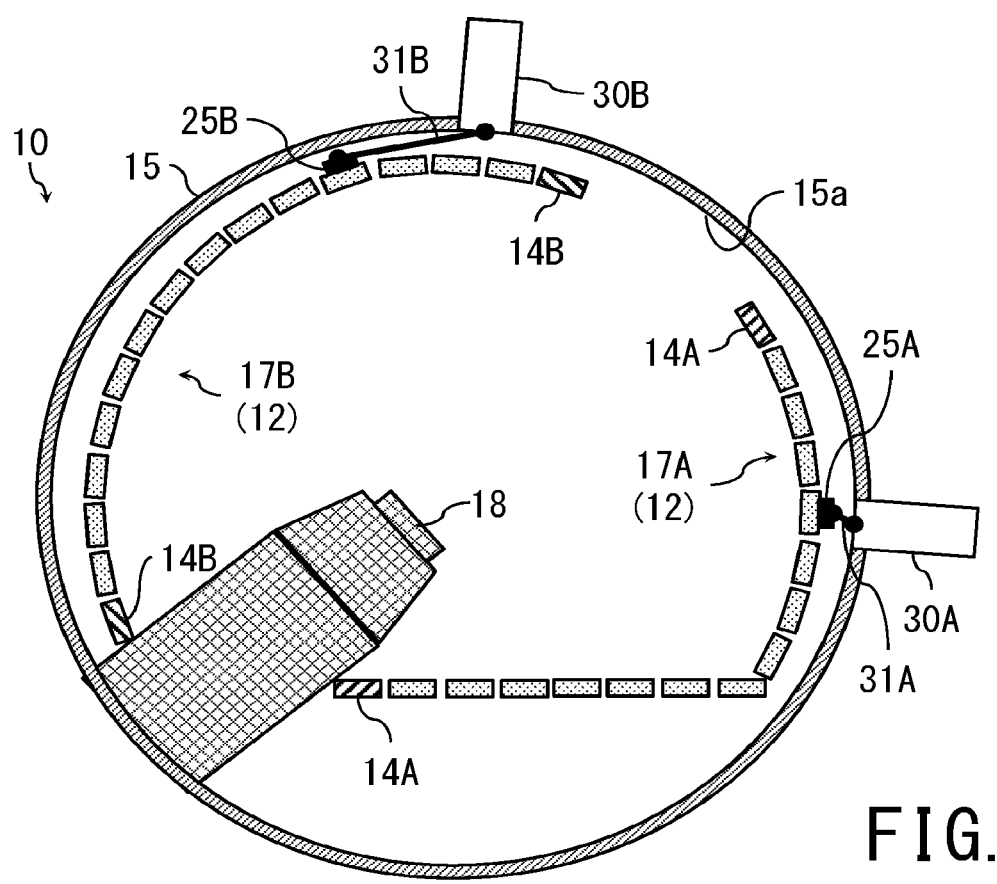
FIG. 8 is still another schematic cross-sectional view illustrating the operation of the moving floor and the cable-length adjusters.

Next, as shown in FIG. 8, consider a case where the rotation angle of the gantry 15 is set to +135° and the irradiation port 18 is positioned obliquely below the bed 24. In this case, by causing the respective edges 14A and 14B of the separate bodies 17A and 17B to contact the side of the irradiation port 18, the horizontal flat floor surface of the moving floor 12 is formed without forming an opening.

In this state, both of the driving devices 25A and 25B are positioned at the arch-shaped ceiling and the cable 31A is almost accommodated in the adjuster 30A, while the cable 31B is almost entirely pulled out from the adjuster 30B so as to be arranged along the circumferential direction.

Figure 9:
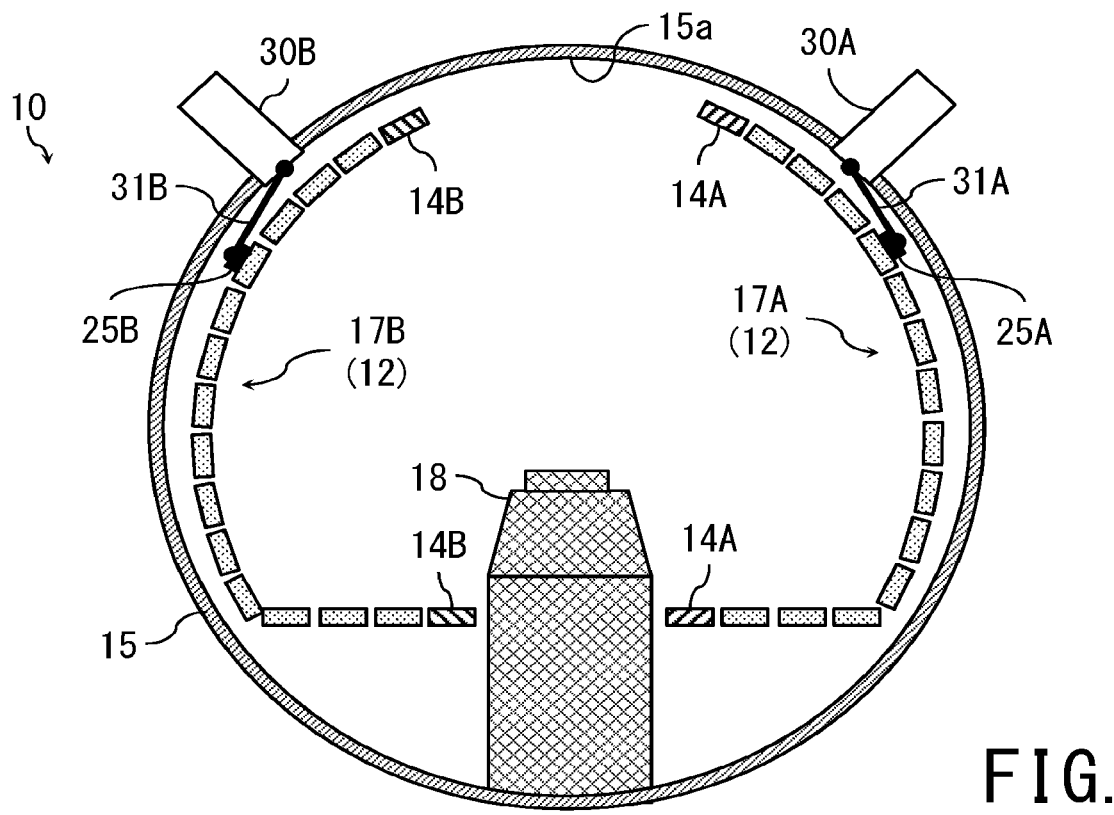
FIG. 9 is still another schematic cross-sectional view illustrating the operation of the moving floor and the cable-length adjusters.

Further, as shown in FIG. 9, consider a case where the rotation angle of the gantry 15 is set to 180° and the irradiation port 18 is positioned directly below the bed 24. Also in this case, by bringing the irradiation port 18 into contact with the respective edges 14A and 14B of the separate bodies 17A and 17B, the horizontal flat floor surface of the moving floor 12 is formed without forming openings on both sides of the irradiation port 18.

In this state, both of the driving devices 25A and 25B are positioned at the arch-shaped ceiling and both of the cables 31A and 31B are almost entirely pulled out from the respective adjusters 31A and 30B along the circumferential direction.

The above-described positional relationship between the irradiation port 18, the separate bodies 17A and 17B, the driving devices 25A and 25B, and the adjusters 30A and 30B is only one aspect, and embodiments of the present invention is not limited to such an aspect. Thus, the positional relationship is appropriately changed depending on, e.g., the length of the arcuate track of the rail 13, the length of the linear track of the rail 13, and the size of the irradiation port 18. Although a description has been given of the case where the gantry 15 rotates in the range of 180° in one direction, the gantry 15 can be rotated in the range of 180° also in the opposite direction.

According to the particle beam treatment apparatus of at least one embodiment as described above, stability of rotating operation can be improved by adjusting the wire length of the cable inside the gantry, which cable is connected to a device provided on the moving floor.

Some embodiments of the present invention have been described above. These embodiments have been presented as examples. There is no intention to limit the scope of the invention. These embodiments can also be implemented in other various modes, and variously omitted, replaced, changed, and combined without departing from the gist of the invention. The embodiments and their variations are encompassed by the scope and gist of the invention. Likewise, these embodiments and variations are encompassed by the invention described in the claims and its range of equivalence.

What is claimed is:

1. A particle beam treatment apparatus comprising:
   a gantry configured to axially rotate in a state where an irradiation port for a beam is fixed to a body of the rotating gantry;
   a moving floor that is provided inside the gantry, is configured by annularly connecting a plurality of plates with each other in a freely bendable manner, accommodates at least a part of a bed fixed to a stationary system, and rotates together with the gantry to cause the irradiation port to penetrate the moving floor;
   a cable configured to be connected to a device fixed to the moving floor and configured to be wired to outside of the gantry, the cable passing through the gantry;
   an adjuster configured to adjust length of the cable wired inside the gantry when the gantry axially rotates;
   wherein the adjuster comprises,
   a casing configured to accommodate the cable and to be provided at such a position of the gantry that the cable penetrates the gantry,
   a wire configured to hold a part of the cable by a tip, and
   a wheel that is provided in the casing, winds the wire from an end of the wire, and rotates in a forward/reverse direction according to displacement of the tip of the wire.

2. The particle beam treatment apparatus according to claim 1, further comprising a rail that includes an arcuate track and a linear track and is slidably engaged with at least one of both ends of the moving floor,
   wherein the moving floor is composed of at least two separate bodies in such a manner that connection of the plurality of plates is divided at a position where the irradiation port penetrates the moving floor; and
   the device is provided for each of the separate bodies and is configured to cause one of the separate bodies to run along the rail.

3. The particle beam treatment apparatus according to claim 1,
   wherein the cable is configured by bundling a plurality of lines connected to respective devices into one and covering bundled lines.

4. The particle beam treatment apparatus according to claim 1,
   wherein the wheel is configured to rotate in such a manner that rotation of the wheel is resiliently biased in a direction in which the wire is wound.

5. The particle beam treatment apparatus according to claim 1,
   wherein rotation of the wheel is driven and controlled.

6. The particle beam treatment apparatus according to claim 1,
   wherein the casing is made of a transparent material in such a manner that shape of the cable to be accommodated can be visually recognized.

* * * * *